(12) United States Patent
Wade et al.

(10) Patent No.: US 10,292,874 B2
(45) Date of Patent: May 21, 2019

(54) DUAL-MODE HIGH-WAIST FOLDOVER DISPOSABLE ABSORBENT PANT

(71) Applicant: The Procter & Gamble Company, Cincinnati, OH (US)

(72) Inventors: Sarah Marie Wade, Springfield Township, OH (US); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 198 days.

(21) Appl. No.: 15/298,565

(22) Filed: Oct. 20, 2016

(65) Prior Publication Data

US 2017/0105884 A1   Apr. 20, 2017

Related U.S. Application Data

(60) Provisional application No. 62/243,971, filed on Oct. 20, 2015.

(51) Int. Cl.
*A61F 13/49* (2006.01)
*A61F 13/496* (2006.01)
*A61F 13/84* (2006.01)

(52) U.S. Cl.
CPC .. *A61F 13/49011* (2013.01); *A61F 13/49001* (2013.01); *A61F 13/496* (2013.01); *A61F 2013/8497* (2013.01)

(58) Field of Classification Search
CPC ............. A61F 13/49058; A61F 13/49011
See application file for complete search history.

(56) References Cited

U.S. PATENT DOCUMENTS

| 3,860,003 | A | 1/1975 | Buell |
| 4,515,595 | A | 5/1985 | Kievet et al. |
| 4,610,678 | A | 9/1986 | Weisman |
| 4,673,402 | A | 6/1987 | Weisman |
| 4,834,735 | A | 5/1989 | Alemany |
| 4,854,984 | A | 8/1989 | Ball |

(Continued)

FOREIGN PATENT DOCUMENTS

WO    WO 1995-16746 A1    6/1995

OTHER PUBLICATIONS

PCT International Search Report, dated Jan. 18, 2017 (12 pages).

*Primary Examiner* — Susan S Su
(74) *Attorney, Agent, or Firm* — William E. Gallagher

(57) ABSTRACT

A dual-mode high-waist disposable absorbent pant with foldover waist features is disclosed. The pant may include a laterally extending folding region disposed longitudinally between the waist opening edge and the front and/or rear ends of an absorbent core structure; the folding region may include a first web structure. The pant may also include a waistband region disposed longitudinally between the waist opening edge and the folding region; the waistband region may include a second web structure and one or a plurality of laterally extending, pre-strained elastic member(s) disposed between a first pair of layers. The second web structure may differ in configuration from the first web structure. The longitudinal dimension between the waist opening edge of the pant and the leg opening edges may be at least 30 percent of the overall length of the pant when in an open, fully extended and flattened condition.

15 Claims, 11 Drawing Sheets

(56) References Cited

U.S. PATENT DOCUMENTS

| | | |
|---|---|---|
| 4,888,231 A | 12/1989 | Angstadt |
| 4,892,536 A | 1/1990 | Des Marais |
| 4,919,738 A | 4/1990 | Ball |
| 4,990,147 A | 2/1991 | Freeland |
| 5,037,416 A | 8/1991 | Allen |
| 5,137,537 A | 8/1992 | Herron |
| 5,147,345 A | 9/1992 | Young |
| 5,151,092 A | 9/1992 | Buell |
| 5,221,274 A | 6/1993 | Buell |
| 5,260,345 A | 11/1993 | Des Marais |
| 5,266,392 A | 11/1993 | Land et al. |
| 5,269,775 A | 12/1993 | Freeland |
| 5,342,338 A | 8/1994 | Roe |
| 5,387,207 A | 2/1995 | Dyer |
| 5,397,316 A | 3/1995 | LaVon |
| 5,554,145 A | 9/1996 | Roe et al. |
| 5,569,234 A | 10/1996 | Buell |
| 5,571,096 A | 11/1996 | Dobrin |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda |
| 5,629,097 A | 5/1997 | McCann |
| 5,635,191 A | 6/1997 | Roe |
| 5,643,588 A | 7/1997 | Roe |
| 5,690,627 A * | 11/1997 | Clear ............... A61F 13/15593 604/385.29 |
| 5,865,823 A | 2/1999 | Curro |
| 5,916,661 A | 6/1999 | Benson |
| 6,004,306 A | 12/1999 | Robles et al. |
| 6,107,537 A | 8/2000 | Elder |
| 6,210,386 B1 * | 4/2001 | Inoue ............... A61F 13/49011 604/385.01 |
| 6,429,352 B1 | 8/2002 | Herrlein |
| 6,632,385 B2 | 10/2003 | Kauschke |
| 6,645,569 B2 | 11/2003 | Cramer |
| 6,677,258 B2 | 1/2004 | Carroll |
| 6,803,103 B2 | 10/2004 | Kauschke |
| 6,863,933 B2 | 3/2005 | Cramer |
| 7,112,621 B2 | 9/2006 | Rohrbaugh |
| 7,307,031 B2 | 12/2007 | Carroll |
| 7,858,544 B2 | 12/2010 | Turi et al. |
| 8,066,685 B2 | 11/2011 | Olson et al. |
| 8,728,051 B2 | 5/2014 | Lu |
| 8,939,957 B2 | 1/2015 | Raycheck et al. |
| 8,979,815 B2 | 3/2015 | Roe et al. |
| 9,216,116 B2 | 12/2015 | Roe et al. |
| 9,216,118 B2 | 12/2015 | Roe et al. |
| 9,326,899 B2 | 5/2016 | Zink et al. |
| 2003/0148684 A1 | 8/2003 | Cramer |
| 2005/0008839 A1 | 1/2005 | Cramer |
| 2005/0027274 A1 * | 2/2005 | Suzuki ............... A61F 13/49001 604/385.01 |
| 2005/0131379 A1 * | 6/2005 | Otsubo ............ A61F 13/49011 604/387 |
| 2006/0047260 A1 * | 3/2006 | Ashton ................ A61F 13/496 604/396 |
| 2006/0106359 A1 * | 5/2006 | Terada ............. A61F 13/49017 604/385.27 |
| 2008/0108964 A1 | 5/2008 | Edwall |
| 2009/0240228 A1 * | 9/2009 | Nonnenmann ... A61F 13/15593 604/385.3 |
| 2010/0040826 A1 | 2/2010 | Autran et al. |
| 2011/0118689 A1 * | 5/2011 | Een ................... A61F 13/49011 604/385.3 |
| 2011/0125122 A1 * | 5/2011 | Thorson ........... A61F 13/15593 604/385.3 |
| 2011/0196327 A1 | 8/2011 | Chhabra et al. |
| 2012/0316528 A1 | 2/2012 | Schill |
| 2012/0316526 A1 | 12/2012 | Rosati |
| 2012/0323204 A1 * | 12/2012 | Poole ................ A61F 13/49014 604/385.3 |
| 2013/0123736 A1 * | 5/2013 | Ichikawa .......... A61F 13/49011 604/385.19 |
| 2013/0281954 A1 * | 10/2013 | Ishihara ............ A61F 13/49011 604/385.3 |
| 2013/0310793 A1 * | 11/2013 | Wade ................ A61F 13/49019 604/385.29 |
| 2013/0317471 A1 * | 11/2013 | Morimoto ......... A61F 13/49012 604/385.3 |
| 2014/0005628 A1 * | 1/2014 | LaVon .................... A61F 13/64 604/392 |
| 2014/0031135 A1 | 1/2014 | Hult et al. |
| 2014/0188067 A1 * | 7/2014 | Herron .................... A61F 13/49 604/385.01 |
| 2014/0336605 A1 | 11/2014 | Hardie et al. |
| 2014/0378934 A1 * | 12/2014 | Takahashi ........ A61F 13/49011 604/385.26 |
| 2015/0073373 A1 * | 3/2015 | Mukai .............. A61F 13/49001 604/385.29 |
| 2015/0083310 A1 | 3/2015 | Wade et al. |
| 2015/0088087 A1 * | 3/2015 | Kawakami ............ A61F 13/496 604/385.16 |
| 2015/0088088 A1 | 3/2015 | Wade et al. |
| 2015/0285308 A1 | 10/2015 | Kanamoto |
| 2016/0015574 A1 * | 1/2016 | Okubo ............. A61F 13/49011 604/385.27 |
| 2016/0100999 A1 * | 4/2016 | Hamilton ......... A61F 13/49011 604/372 |
| 2017/0049637 A1 * | 2/2017 | Mori ................. A61F 13/49011 |
| 2017/0056257 A1 * | 3/2017 | Nishikawa ....... A61F 13/49011 |
| 2017/0231839 A1 * | 8/2017 | Tashiro ................ A61F 13/515 604/385.3 |

* cited by examiner

DUAL-MODE HIGH-WAIST FOLDOVER DISPOSABLE ABSORBENT PANT

BACKGROUND OF THE INVENTION

The business of manufacturing disposable absorbent pants is highly capital intensive and highly competitive at the present time. In the market for such articles for toddlers and young children, it is not uncommon for the manufacturer to offer four, five or more sizes collectively adapted to satisfy the expected period of need for children in the market, e.g., from about age 18 months to about age 3 years. As will be understood, body sizes vary greatly for children in this age range. Typically, manufacture of each size pant requires its own separate manufacturing line, which requires a substantial capital investment for the manufacturer.

Consequently, there is room for any improvement that enables a reduction in the number of pant sizes the manufacturer needs to offer to serve its market. Any incidental improvements that benefit the consumer are welcome as well.

DESCRIPTION OF EXAMPLES

Definitions

Figure 1:
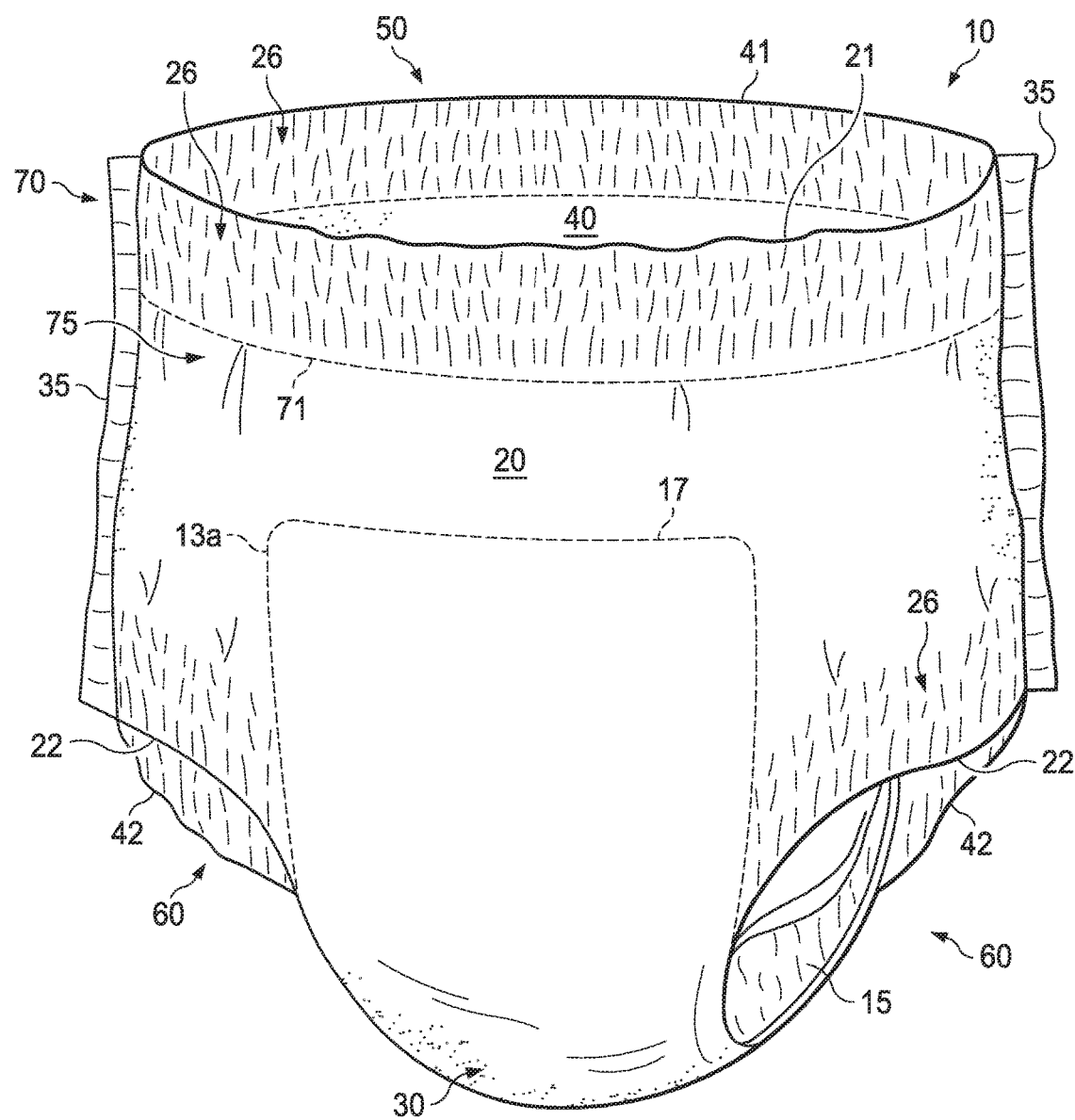
FIG. 1 is a perspective view of an example of a disposable absorbent pant in high-waist mode.

The following definitions of the following terms apply for purposes herein:

"Absorbent article" means a disposable diaper or disposable absorbent pant.

"Cross direction" (CD)—with respect to the making of a nonwoven web material, the nonwoven material itself, a laminate thereof, or an article in which the material is a component, refers to the direction along the material substantially perpendicular to the direction of forward travel of the material through the manufacturing line in which the material and/or article is manufactured.

Throughout the present description, a material or composite of materials is considered to be "elastic" or "elastomeric" if, when a biasing force is applied to the material, the material or composite can be extended to an elongated length of at least 150% of its original relaxed length (i.e. can extend at least 50%), without rupture or breakage which substantially damages the material or composite, and when the force is removed from the material or composite, the material or composite recovers at least 40% of such elongation. In various examples, when the force is removed from an elastically extensible material, the material or composite may recover at least 60% or even at least 80% of its elongation.

"Film" means a skin-like or membrane-like layer of material formed of one or more polymers, which does not have a form consisting predominately of a web-like structure of consolidated polymer fibers and/or other fibers.

"Fine fibers" means fibers having an average diameter of 0.10 µm to 10 µm. Fine fibers may be produced by processes including, for example, meltblowing processes.

The "front waist region" of an absorbent article is the portion of the article extending longitudinally from the front waist edge to a lateral line tangent to both the left and right front leg edges, and closest to the front waist edge.

The "rear waist region" of an absorbent article is the portion of the article extending longitudinally from the rear waist edge to a lateral line tangent to both the left and right rear leg edges and closest to the rear waist edge.

The "crotch region" of an absorbent article is the portion of the article lying longitudinally between the front waist region and the rear waist region.

With respect to a pant precursor structure or diaper in an opened configuration, laid out flat and stretched out to its full dimensions against any contraction induced by included elastic members, the "longitudinal" direction is the direction perpendicular to the waist edges, and the "lateral" direction is the direction parallel to the waist edges. With respect to a wearer, the "longitudinal" direction is the direction parallel to the wearer's standing height, and the "lateral" direction is the direction perpendicular to the wearer's standing height and extending along the left-right direction relative to the wearer. References to a "length" dimension refer to a dimension measured in the longitudinal direction; references to a "width" dimension refer to a dimension measured in the lateral direction.

"Machine direction" (MD)—with respect to the making of a nonwoven web material, the nonwoven material itself, or a laminate thereof, refers to the direction along the material or laminate substantially parallel to the direction of forward travel of the material or laminate through the manufacturing line in which the material or laminate is manufactured.

"Machine direction bias," with respect to the fibers forming a nonwoven web, means that a majority of the fibers, as situated in the web and unstretched, have lengths with machine direction vector components that are greater than their cross direction vector components.

A "nonwoven" is a manufactured sheet or web of directionally or randomly oriented fibers which are first formed into a batt and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural and/or man-made origin and may be staple and/or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm).

With respect to a connection between two discrete sections of material (such as a seam), "permanent" means that the sections are joined in such a manner and/or by such a mechanism that a forcible separation of the materials at the connection cannot occur without substantial damage to the article and/or the materials cannot be rejoined at the connection (without unusual measures) to substantially restore the pre-separation configuration and structural integrity of the article. Non-limiting examples of mechanisms by which a permanent connection may be formed include adhesive and thermal bonding between the sections. Conversely, a "refastenable" connection joins the sections in such a manner and/or by such a mechanism that a forcible separation of the materials at the connection can occur without substantial damage to the article, and the materials can be rejoined at the connection (without unusual measures) to substantially restore the pre-separation configuration and structural integrity of the article. A non-limiting example of mechanisms by which a refastenable connection may be formed includes inclusion of hook-and-loop fastening system component(s) to join the sections.

"z-direction" means the direction orthogonal to an x-y plane occupied or approximately defined by a pant precursor structure when laid out flat; and also means the direction orthogonal to the wearer's body surfaces (i.e., orthogonally toward or away from the wearer's body surfaces) when the pant is worn, in areas of the wearer's body covered by the pant. "z-direction," with respect to a web, means generally orthogonal or perpendicular to the plane approximated by the web along the machine and cross direction dimensions.

All dimensions, dimensional relationships and surface areas that are referred to herein are measured with the absorbent article (or subject component thereof) opened (separated at side seams if necessary), laid out horizontally on a flat surface, and extended out to its full dimensions against any contraction induced by the presence of pre-strained elastic members.

Figure 2:
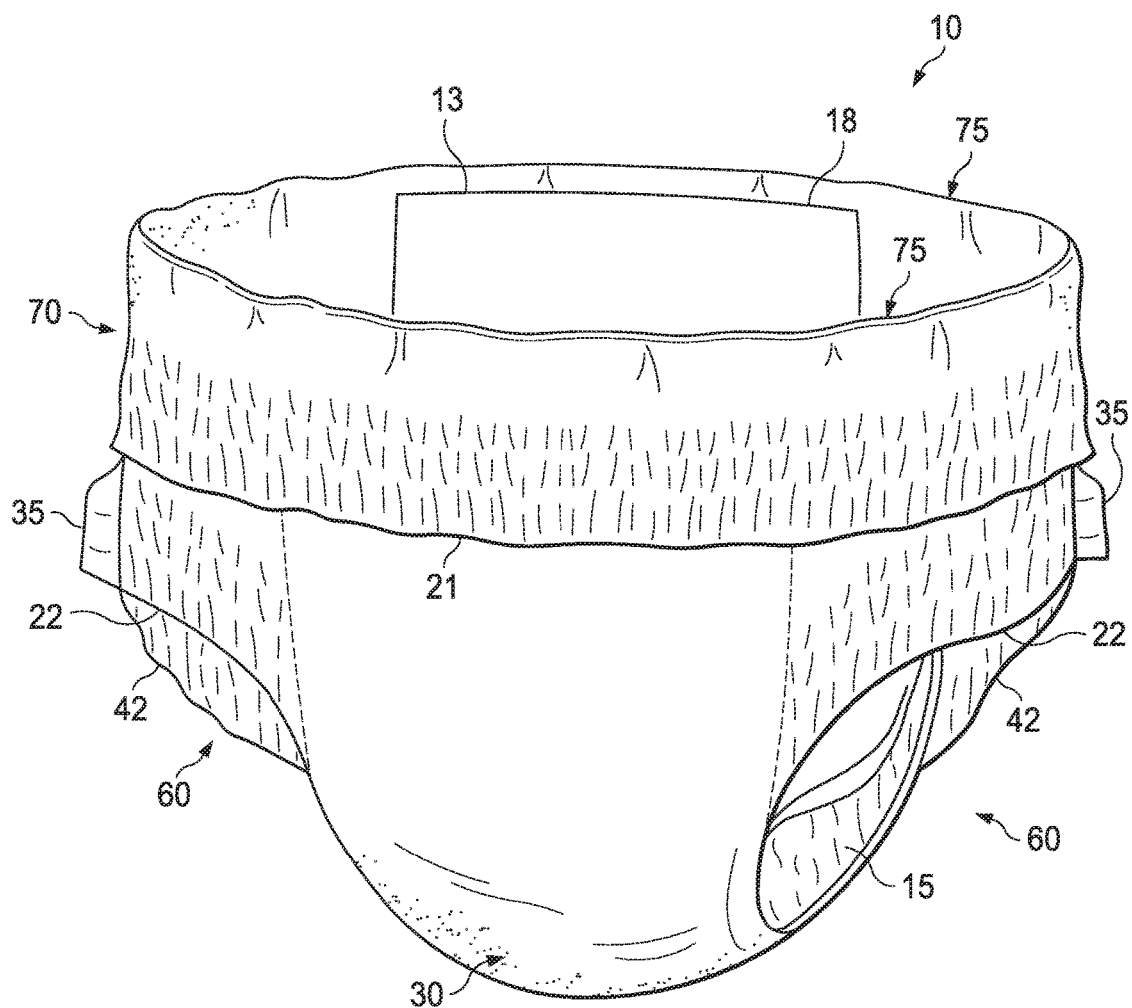
FIG. 2 is a perspective view of an example of the disposable absorbent pant of FIG. 1, in foldover mode.

FIG. 1 is a perspective view of an example of a disposable absorbent pant 10 shown in its full-length, high-waist mode. FIG. 2 is a perspective view of the pant 10 of FIG. 1 shown in foldover mode, in which a waistband region 70 of each of front waist region 20 and rear waist region 40 has been folded outwardly and down along a folding region 75, thereby shortening the pant structure to more resemble a brief, and increasing tension through the waistband region 70 when the pant is worn.

Figure 3:
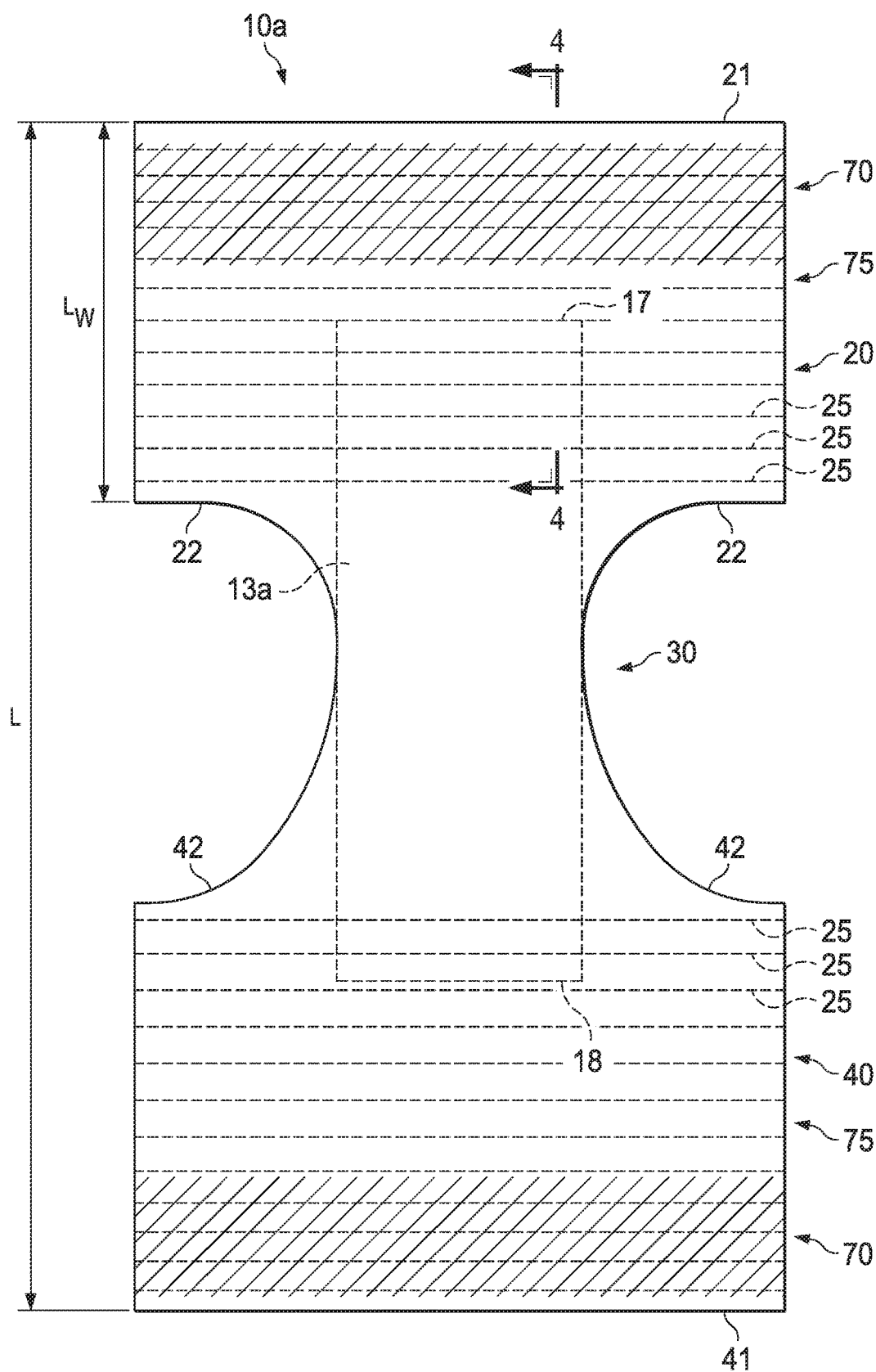
FIG. 3 is schematic plan view of an example of a precursor structure of a disposable absorbent pant, with outward-facing surfaces thereof facing the viewer.
Figure 4A:
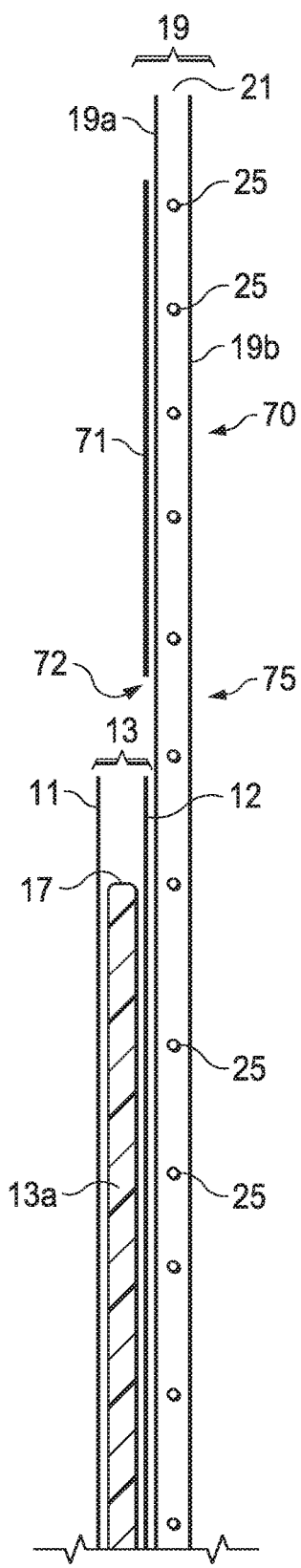
FIGS. 4A-4C are schematic longitudinal cross-sectional, exploded views of alternative configurations of the front portion of the structure of FIG. 3, taken through line 4-4 shown in FIG. 3.
Figure 4B:
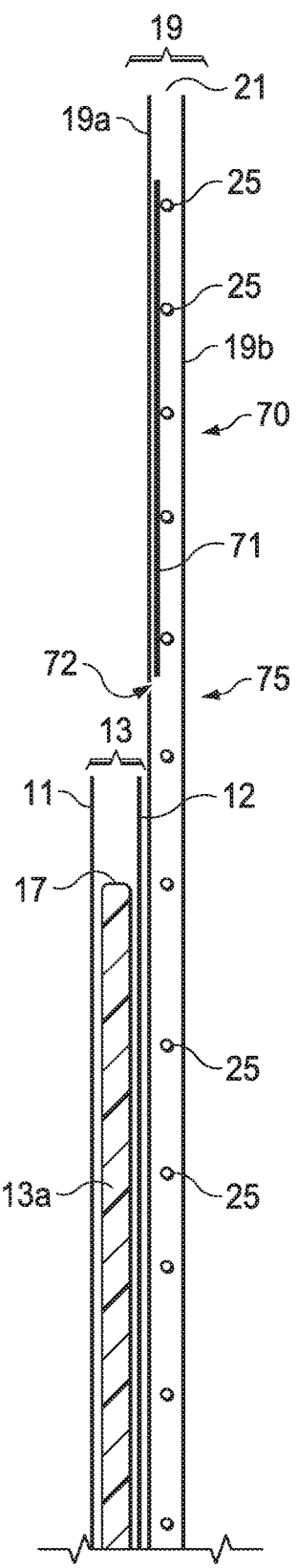
Figure 4C:
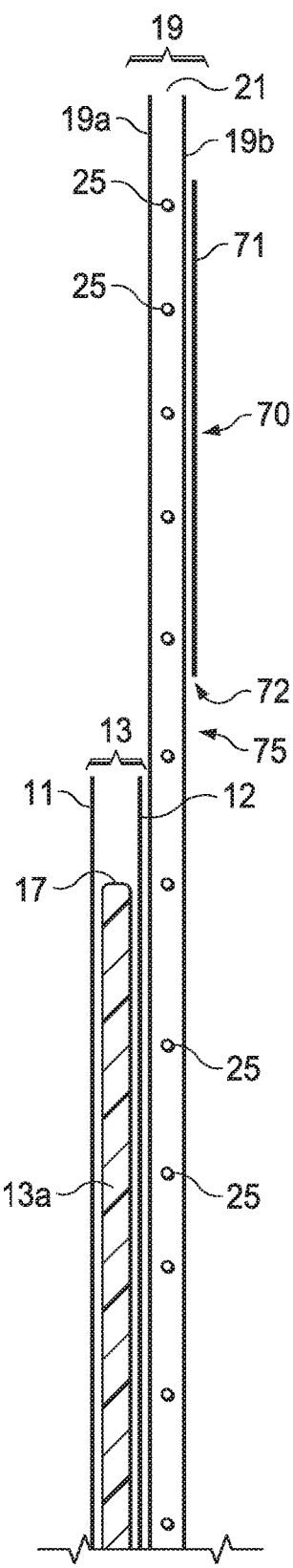

FIG. 3 is schematic plan view of an example of a precursor structure of a disposable absorbent pant, with outward-facing surfaces thereof facing the viewer. FIGS. 4A-4C are schematic longitudinal cross-sectional, exploded views of alternative configurations of the structure of FIG. 3, taken through line 4-4 shown in FIG. 3.

A pant 10 and its precursor structure 10a will have a front waist region 20, crotch region 30 and rear waist region 40, identified as such by the portions of the wearer's lower torso that they cover when the pant is worn. The pant structure will have lateral front waist edge 21 and lateral rear waist edge 41 defining a waist opening 50. The pant structure will have a pair of front leg edges 22 and a pair of rear leg edges 42 respectively defining a pair of leg openings 60. To form a finished pant 10, the precursor structure 10a may be folded laterally to bring respective waist edges 21, 41 toward each other, and the materials respectively forming the front and rear waist regions 20, 40 of precursor structure 10a may be joined by side seams 35 to form a pant structure. Side seams 35 may be permanent (as exemplified by side seams of current PAMPERS EASY UPS children's training pants (product of The Procter & Gamble Company, Cincinnati, Ohio), in which respective materials of the front and rear waist regions are thermally bonded together, or refastenable (as exemplified by side seams of current HUGGIES PULL-UPS children's training pants (product of Kimberly Clark Corporation, Irving, Tex.), in which respective materials of the front and rear waist regions are joined by a reusable mechanical fastening system (hook and loop system).

Referring to FIGS. 4A-4C, pant 10 may have an outer chassis structure 19 and a central chassis structure 13. Central chassis structure 13 may include a liquid permeable topsheet 11, a liquid impermeable backsheet 12, and an absorbent core structure 13a disposed between the topsheet and backsheet. The perimeter of the absorbent core structure 13a (in plan view) is defined by the outer edges of deposits of absorbent materials (e.g., superabsorbent polymer particles) and/or liquid distributing materials (e.g., cellulose pulp fibers) included therein to serve the function of distributing liquid exudate (typically, urine) along the absorbent material(s) and/or absorbing and storing it until the time the pant is removed from the wearer and discarded. The topsheet 11 and backsheet 12 may be joined about their perimeters by, e.g., a pattern of thermal bonds and/or adhesive (not shown), to form an enveloping structure that contains the absorbent core structure 13a. Central chassis 13 may have a pair of longitudinal cuff structures (not specifically shown). Cuff structures may include integral or separate barrier cuffs 15 (FIG. 1) and leg cuffs (not specifically shown). Barrier cuffs may be configured so as to extend away from the pant structure and toward the wearer's body surfaces through the crotch region in the z-direction when the pant is worn, so as to help contain the wearer's exudates. Leg cuffs may be configured to cause the pant to fit snugly about the wearer's legs.

Non-limiting examples of suitable configurations of topsheet, backsheet, absorbent core structure and barrier cuffs are described in in U.S. patent application Ser. No. 13/764,945.

In one configuration reflected in FIGS. 4A-4C, outer chassis structure 19 of pant 10 may include an elasticized belt configuration. An elasticized belt configuration may be formed, for example, by a plurality of longitudinally-spaced elastic strands 25 extending laterally across the front and rear waist regions, sandwiched between two outer chassis layers 19a and 19b. Elastic strands 25 may be disposed to the outside of the backsheet 12, and may be affixed in place at side seams 35 and/or along their lateral lengths by, e.g., strand-coating with adhesive during manufacture, or otherwise by a pattern of adhesive applied to the backsheet during manufacture of the pant. Elastic strands 25 may be incorporated into the structure in a pre-strained condition, such that, upon completion of manufacture of the pant, and relaxation of the structure, the elastic strands 25 are allowed to contract, laterally drawing the layers 19a, 19b to form ruffles or gathers of material 26 (FIG. 1). The gathers and pre-strained elastic strands impart the waist regions with elastic stretch capabilities, facilitating donning and removal of the pant and providing for snug and secure fit during wear.

As an alternative to or substitute for elastic stands 25, elasticity may be provided by one or more strips of elastic film, pre-strained in the lateral direction.

Foldover Features

The pant 10 and/or the outer chassis structure 19 may be imparted with features that provide for two modes of wear, high-waist mode (as suggested by FIG. 1) and foldover mode (as suggested by FIG. 2). The features described herein enable the consumer to fold the waistband region outwardly and down over the waist regions to configure the pant in foldover mode, in a manner such that a consistently-sized foldover mode is easily tactilely and visually identified, and stably retained during wear (i.e., the folding location and foldover size of the pant are substantially maintained such that the folded-over portion does not substantially shift, or reduce or increase in longitudinal dimension during wear).

A folding region 75 may extend laterally across each of the front and rear waist regions 20, 40. The folding region 75 in the front and rear waist region 20, 40 is the location about which the waistband region 70 (in FIGS. 3 and 6, indicated by lateral bands of cross-hatching) will naturally fold down if desired by the consumer. It is bounded along the bottom by the front and rear ends 17, 18 of the absorbent core structure; and bounded at the top by a lower edge of the waistband region 70. Generally, the folding region 75 may be tactilely identified as a laterally extending band of material in the waist region having lesser bending stiffness (stiffness is resistance to bending along a lateral line), than either the region including the absorbent core structure 13a, or the waistband region 70. As such, it is a laterally extending region along which the pant naturally will tend to fold about a lateral line, and remain folded generally along the same lateral line or laterally extending band of material during wear.

In order to ensure that the folding region is effectively detectable tactilely and effective at maintaining the foldover configuration with relatively consistent dimensions during wear, it may be desired that the difference in bending stiffness between the folding region 75 and the waistband region 70 be at a minimum. Accordingly, it may be desired that the bending stiffness of the waistband region be at least 20 percent greater than the bending stiffness of the folding region, more preferably at least 30 percent greater, and even more preferably at least 40 percent greater, as measured by the Bending Stiffness method set forth below.

The difference in bending stiffness between waistband region 70 and folding region 75 may be imparted by any one or a combination of several elements.

In one example, waistband region 70 may include an added stiffening layer 71, which includes additional material not present in at least a portion of or the entirety of the folding region 75. Stiffening layer 71 may be formed of a section of one or more layers of nonwoven web material; by a section of elastic or inelastic film; or by a laminate thereof. Alternatively, stiffening layer 71 may be laminate of a section of nonwoven web material laminated with one or more laterally pre-strained elastic members (formed of, e.g., elastic film or elastic strands), thereby providing elastic stretch and supplemental tension in the waistband region. Stiffening layer 71 is provided with a lower lateral edge 72, which may define the lower boundary of the waistband region 70 and the upper boundary of the folding region 75. As suggested in FIGS. 4A-4C, stiffening layer 71 may be disposed to the inside (wearer-facing side) of the outer chassis structure (FIG. 4A); between layers of the outer chassis structure (FIG. 4B); or to the outside of the outer chassis structure (FIG. 4C). The comparatively lesser bending stiffness of the folding region 75 facilitates folding laterally thereabout to the foldover mode, reflected in FIGS. 2 and 5.

In another example, the desired stiffness difference may be the result of localized basis weights that differ between the waistband region and the folding region. Although not necessarily true in every case, for materials of the type used in construction of pants of the type contemplated herein, a region having greater basis weight (of all materials and layers included in the region) may generally have a greater bending stiffness than a region having a lesser basis weight. Accordingly, it may be desired that the basis weight of all materials present in a localized area of the waistband region 70 be at least 30 percent, more preferably at least 40 percent, and even more preferable at least 50 percent greater than the basis weight of all materials present in a localized area of folding region 75. (Herein, basis weight is the weight of all materials present in the area of interest, divided by the plan surface area of the area of interest.)

It will be appreciated that high waist mode, reflected in FIG. 1, enables the pant 10 to accommodate larger wearers within the designed size range for the pant. High waist mode provides for a greater amount of body coverage, and a lesser amount of lateral tension through the waist regions. Conversely, foldover mode, reflected in FIG. 2, enables the pant 10 to accommodate smaller wearers within the designed size range for the pant. It provides for a lesser amount of body coverage (where greater coverage is not needed and/or is not desirable due to the smaller size of the wearer). Additionally, the multiplication of material thickness and tension about the waist regions resulting from the folding over and superimposition of waistband region and areas below the waistband region provides for increased snugness and fit security for the smaller wearer. Thus, the consumer may benefit from being able to purchase larger quantities of one size pant that will be suitable for a greater period of wearer growth. The manufacturer may benefit from being able to serve its market with fewer manufactured sizes (necessitating fewer manufacturing lines), because each size pant can accommodate a greater range of wearer sizes. In addition, or alternatively, some consumers may prefer the flexibility of a product providing for two modes of wear, having respectively differing appearances, coverages and fit characteristics.

In order to strike a balance between waist edge heights in respective high-waist and foldover modes appropriate for wearing, it may be desired that the pant be sized according to certain criteria. Thus, referring to FIG. 3, it may be desired that each waist region have a longitudinal dimension Lw that is no less than 30 percent of the overall length L of the pant precursor structure 10a, front waist edge 21 to rear waist edge 41. Herein, Lw is measured between the waist edge and the upper extent of a leg edge, as suggested in FIG. 3.

Figure 7A:
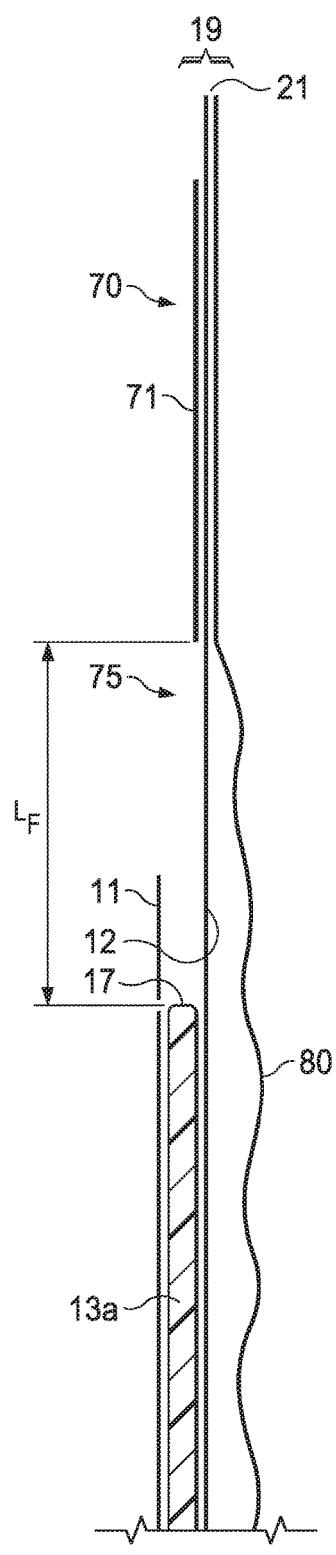
FIGS. 7A-7C are schematic longitudinal cross-sectional, exploded views of alternative configurations of the front portion of the structure of FIG. 6, taken through line 7-7 shown in FIG. 6.

Additionally, to ensure that the edges of the waist opening have a relatively neat appearance in foldover mode, it may be desired that the longitudinal dimension of the folding region 75 be limited. Thus, it may be desired that the folding region have a longitudinal dimension LF no greater 60 mm, more preferably no greater than 40 mm, and even more preferably greater than 25 mm. Herein, dimension LF is measured from the proximate front or rear end 17 or 18 of the absorbent core structure 13*a* to the bottom edge of stiffening layer 71, as illustrated in FIG. 7A.

Figure 5:
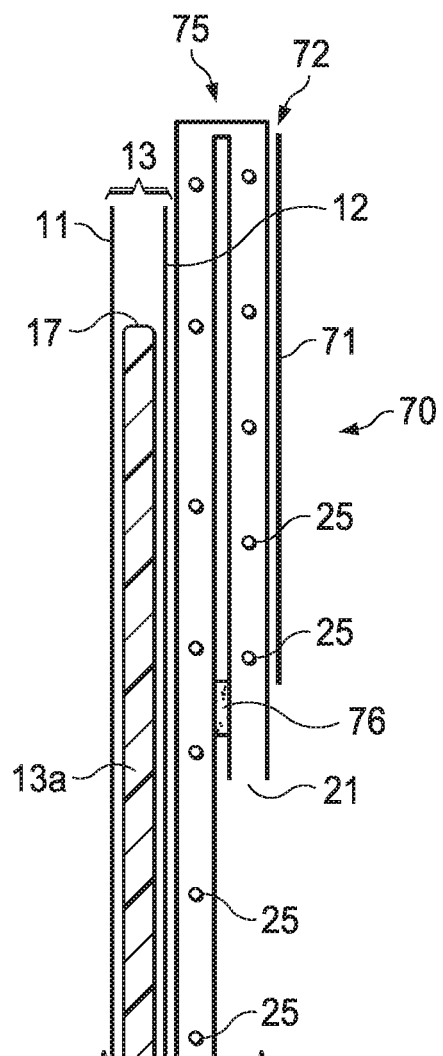
FIG. 5 is a view of the alternative configuration shown in FIG. 4A, shown in foldover mode.
Figure 8:
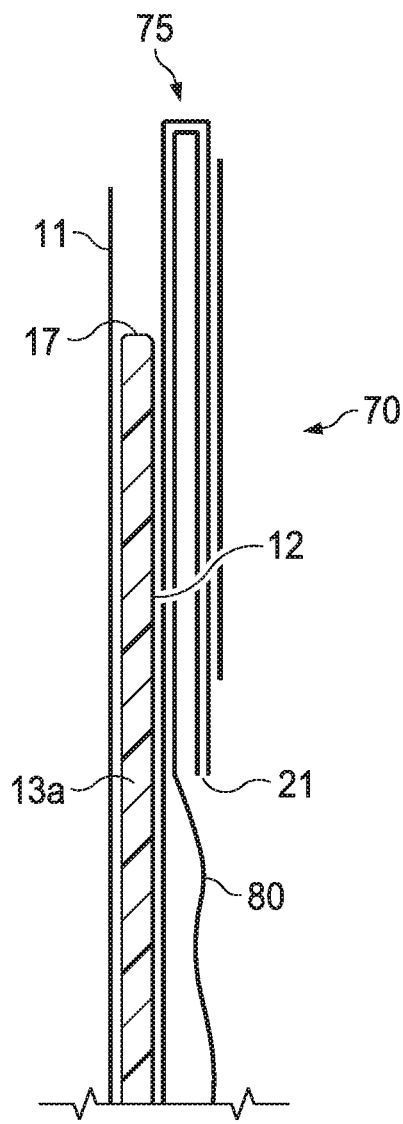
FIG. 8 is a view of the alternative configuration shown in FIG. 7A, shown in foldover mode.

In conjunction with the above features, it may be desired that the topsheet 11 and/or backsheet 12 of the central chassis 13 have forward and rearward ends that lie longitudinally short of the waistband region, and more preferably short of the fold through the folding region 75 when the pant is in foldover mode, as suggested in FIGS. 5 and 8. This dimensional feature ensures that the topsheet and/or backsheet do not fold over with the waistband region 70, or otherwise extend above the fold, and thereby contribute to a sloppy or haphazard appearance along the waist edge fold when the pant in foldover mode. If desired, additional stiffening materials (not shown) may be added to the outer chassis structure above the absorbent core structure 13*a*, to better define a zone of relatively lower stiffness of the folding region 75 at its lower portions and encourage formation of the fold with an unfolded margin of material extending above the ends of the absorbent core structure 13*a*.

In conjunction with the features described above, it may be desired to include visible indicia in or on the pant effective to indicate to the consumer the presence and/or location of the waistband and folding regions. In one example, the waistband region may be made visually distinguishable from the folding region by suitably designed printed graphics disposed to be most visible from outside the pant 10 when in high-waist mode. For example, the graphics may change noticeably in color, pattern or visual content along a lateral line approximately aligned with the lower edge of the waistband region.

In addition or in another alternative, the inner/wearer-facing surfaces of the outer chassis (in high-waist mode) may include visual graphic designs that are most visible from those surfaces, and not highly visible from outside the pant in high-waist mode. However, when the pant is placed in foldover mode, such designs are most visible and best seen and most visible from the outside of the pant.

In addition or in another alternative, the pant may be provided with a foldover securing mechanism that secures the folded-over portion in place on the pant in foldover mode. Referring to FIG. 5, for example, a foldover securing mechanism 76 may be disposed between the upper portion of the waistband portion 70 and the underlying portion of the outer chassis structure 19 or central chassis 13, when the pant is in foldover mode. Foldover securing mechanism may be any suitable mechanism that effects a connection, for example, a hook-and-loop fastening system, a compatible adhesive-substrate system, an adhesive-cohesive system, etc., effective to permanently or refastenably attach at least a portion of the waistband region outer surfaces to outward/garment-facing surfaces therebelow on the pant, after the waistband region is folded over.

Another feature that may be included is a contraction ratio differential between the materials forming the folding region and the materials forming the waistband region. Generally, it may be desired that the waistband region contract to a greater extent under the influence of prestrained elastics, than the folding region. This helps ensure that the waistband region provides a snug fit about the wearer's waist and a more relaxed and comfortable fit therebelow, whether the pant is in high-waist mode or foldover mode. For this purpose, it may be desired that the waistband region have a contraction ratio that is at least 10 percent greater, more preferably at least 20 percent greater, and still more preferably at least 30 percent greater, than the contraction ratio of the folding region 75. For purposes herein, the contraction ratio of the waistband region and folding region are measured using the Contraction Ratio method set forth below.

Blouse Layer

Figure 6:
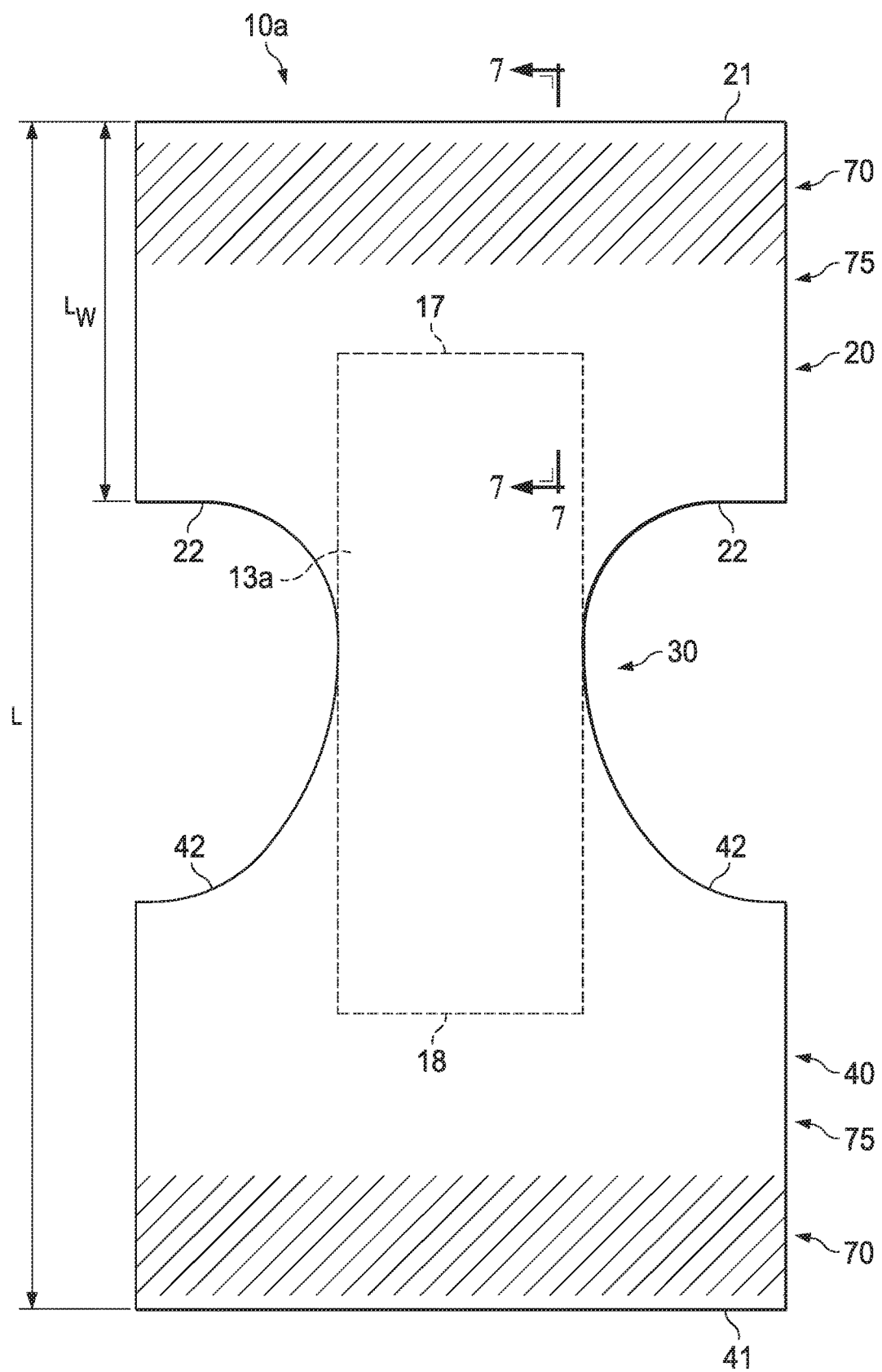
FIG. 6 is schematic plan view of another example of a precursor structure of a disposable absorbent pant, with outward-facing surfaces thereof facing the viewer.
Figure 7B:
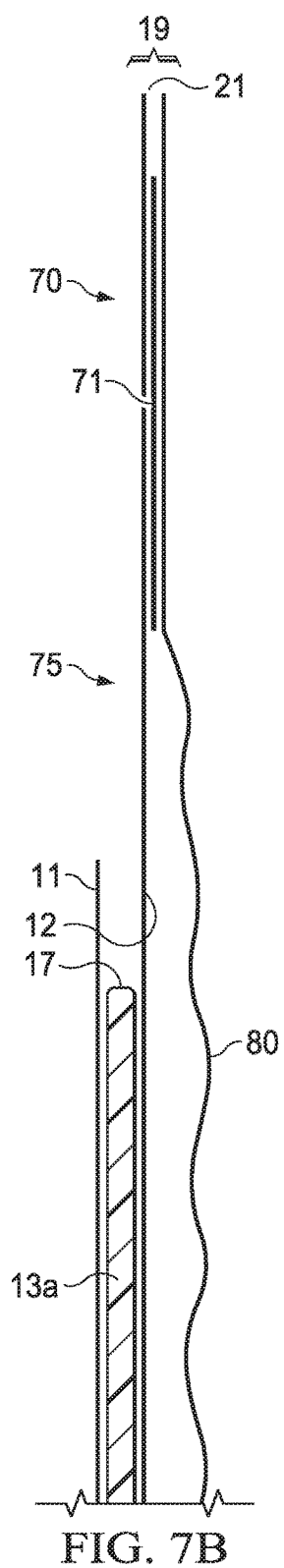
Figure 7C:
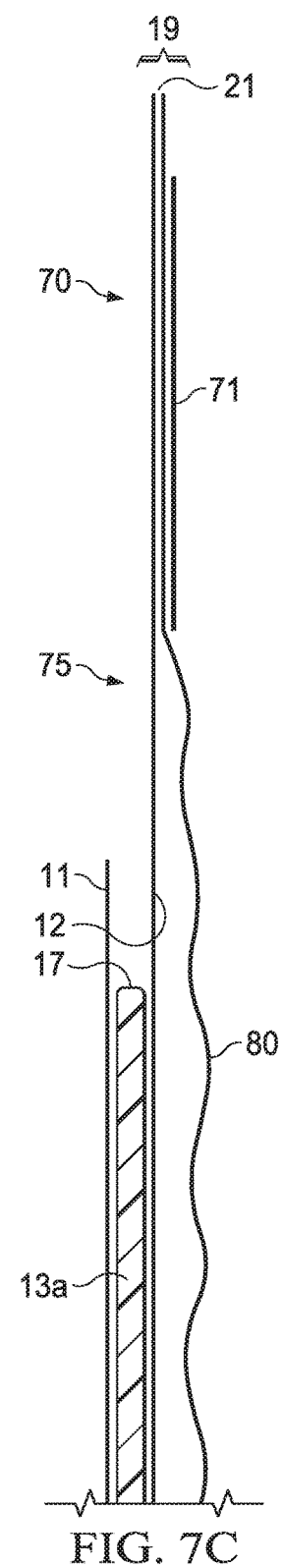

As reflected in FIGS. 6-8, the pant may be provided with an outer blouse layer 80, as described in the application filed contemporaneously herewith, entitled ABSORBENT ARTICLE HAVING AN OUTER BLOUSE LAYER, by Wade.

Outer Chassis Nonwoven Materials

Each of the layers forming outer chassis 19 (e.g. layers 19*a*, 19*b*) may be formed of nonwoven web. Suitable nonwoven web materials that may be useful in the present invention include, but are not limited to spunbond, spunlaid, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, typically used as components of disposable diapers and disposable absorbent pants. The nonwoven web may be formed predominately of polymeric fibers. In some examples, suitable non-woven fiber materials may include, but are not limited to polymeric materials such as polyolefins, polyesters, polyamide, or specifically, polypropylene (PP), polyethylene (PE), poly-lactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in co-pending U.S. patent application Ser. Nos. 10/338,603; 10/338,610; and 13/005,237.

The individual fibers may be monocomponent or multi-component. The multicomponent fibers may be bicomponent, such as in a core-and-sheath or side-by-side arrangement. Often, the individual components comprise polyolefins such as polypropylene or polyethylene, or their copolymers, polyesters, thermoplastic polysaccharides or other biopolymers.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. According to one example, the fibers may include bicomponent fibers, which are individual fibers each comprising different materials, usually a first and a second polymeric material. It is believed that the use of side-by-side bi-component fibers is beneficial for imparting a spiral curl to the fibers.

To enhance loft and promote perceptions of softness of the blouse layer, the nonwoven may be treated by hydrojet impingement, which may also be known as hydroenhancement, hydroentanglement or hydroengorgement. Such nonwovens and processes are described in, for example, U.S. Pat. Nos. 6,632,385 and 6,803,103, and U.S. Pat. App. Pub. No. 2006/0057921, the disclosures of which are incorporated herein by reference.

Other examples of nonwoven web that may be useful for the blouse layer may be an SMS web (spunbond-meltblownspunbond web) made by Avgol Nonwovens LTD, Tel Aviv, Israel, under the designation XL-S70-26; a softband SSS (spunbond-spunbond-spunbond) web made by Pegas Nonwovens AS in Znojmo, Czech Republic, under the designation 18 XX 01 00 01 00 (where XX=the variable basis weight); an SSS web made by Gulsan Sentetik Dok San VE TIC AS, in Gaziantep, Turkey, under the designation SBXXF0YYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width); and a bicomponent SS web.

A nonwoven web useful as a component to form a blouse layer may be pre-bonded, prior to downstream processing such as aperturing as described below. A batt of fibers may be calendered and pre-bonded in a pattern, to consolidate the batt/fibers and create a pattern of bonds that adds tensile strength and dimensional stability, converting the batt of fibers to a coherent and useable nonwoven web material. The web may be imparted with a pattern of pre-bonding as described in, for example, U.S. Pat. No. 5,916,661 (pre-bonding in a pattern of "point calendered bonds 200 to form a coherent web structure") and co-pending U.S. application Ser. No. 13/893,405 (pattern of "primary fiber bonds"). The pre-bonding may consist of a pattern of thermal bonds, mechanical bonds or adhesive bonds, although in some circumstances thermal bonding may be preferred.

Apertured topsheets have been included in absorbent articles of the type described herein. Creating apertures in nonwoven material used to form a topsheet enhances its ability to allow aqueous liquid exudates to pass therethrough. In some circumstances this may be desired because materials of which topsheets are often formed may include polymers (such as polyolefins) that are normally hydrophobic, and pores or passageways ordinarily present between the nonwoven fibers may be insufficiently large to allow aqueous liquids to pass therethrough at a desired rate because the material tends to repel aqueous liquid.

An example of a process for creating apertures in a pre-bonded nonwoven web to be used to form a blouse layer is described in U.S. Pat. Nos. 5,916,661 and 5,629,097. This process involves rolling the pre-bonded nonwoven web through the nip between a pair of rollers, one of which bears a pattern of raised bonding protrusions, and supplying heating energy to heat the fibers beneath the protrusions in the nip. When appropriately controlled pressure and heating energy are provided at the nip, a pattern of suitable bonds or "weakened, melt-stabilized locations" having rod shapes or other shapes results. At the bond sites, the polymer fibers of the web are melted, compressed and thereby fused, such that the fused polymer material at the bond sites is relatively thin (in the z-direction) and frangible. Upon subsequent cross direction incremental stretching of the bonded nonwoven web as described in the above-cited patents, the material at the bond sites or "melt-stabilized locations" breaks and apertures open in a direction transverse to the long dimension of the rod shapes. For example, as described in U.S. Pat. App. Pub. No. 2015/0083310, a nonwoven web may be thermal/calender bonded with a bonding pattern of rod shapes having their long dimension oriented in the machine direction. Following such bonding, the web may be subjected to an incremental stretching process to stretch the web in the cross direction. When the bonding process has been appropriately controlled to create relatively thin, frangible bond sites, this causes the rod-shaped bonds to break open, creating apertures through the web. Advantageously, fibers of the nonwoven web along the edges of the apertures are fused as a result of the bonding process. In comparison to a process in which apertures are simply punched or cut through the web without application of heating energy, the bonding/stretching process described in the above-cited reference does not cut the fibers, which can result in loose fibers and fraying about the edges of the punched or cut apertures. Rather, the bonding/stretching process described tends not to create loose fibers, and provides more neatly defined edges about the apertures. Following incremental stretching, the web may be allowed to relax, which may cause the apertures to close to some extent, but they will still be present.

In another example, the web may be bonded by compression bonding without the application of externally-produced or additional heating energy. Examples of suitable compression bonding systems utilizing rollers are described in, for example, U.S. Pat. Nos. 4,854,984 and 4,919,738. In these types of mechanisms, a first roller and second roller are arranged with their axes in parallel and urged together to form a nip. The first roller may have on its surface one or more bonding protrusions arranged in a pattern. The first roller and second roller may be urged together by one or more actuators such as bellows-type pneumatic actuators acting directly or indirectly on one or both of their axles, to provide and regulate compression, beneath the protrusions at the nip, of the web material as it passes therethrough, in the manner described in the aforementioned patents. A compression bonding mechanism such as, but not limited to, the mechanism described in the aforementioned patents, provides bonding of a nonwoven web material through rapid compression of superimposed fibers beneath the bonding protrusions, along the roller nip line. Without intending to be bound by theory, it is believed that rapid compression beneath the protrusions causes the respective materials to be rapidly deformed and partially expressed together from beneath the protrusions, to form structures of deformed, compressed and entangled fiber material beneath and/or around the protrusions. Welds or weld-like structures at or about the protrusions result. In some circumstances compression bonding provides advantages, including relative simplicity and cost effectiveness. It may reduce or eliminate the need for more complex bonding systems that require a system to supply externally produced or additional heating energy. Without intending to be bound by theory, it is believed that these advantages are substantially independent of variations in line speeds in at least some circumstances, including line speeds within currently known economically and technically feasible ranges for manufacture of disposable diapers and training pants. Following such creation of compression bonds, the web may be incrementally stretched to create apertures at the bond sites, in the manner taught by U.S. Pat. No. 5,916,661.

As noted, as suggested in U.S. Pat. No. 5,916,661, prior to aperturing, the nonwoven web may be pre-bonded with a relatively dense pattern of thermal/calender bonds. Following that, a pattern of apertures may simply be punched or cut through the web. A relatively dense pattern of bonding can serve to minimize loose cut fibers and fraying, and help maintain defined edges of apertures formed by cutting or punching.

It will be appreciated that the apertures created need not necessarily be rod-shaped. Other examples of shapes and patterns are described in co-pending application Pub. No. US 2014/0336605. The apertures may be rod-shaped, arc-shaped, other curved finite paths, circular, oval, elliptical or polygon, and any combinations thereof. It may be desired in some circumstances as suggested in the figures, however, that the longest dimension of a majority of the individual apertures be oriented along the machine direction of the nonwoven web—particularly when the web or components of it are formed by processes that produce a machine direction bias in the fibers such as spunbonding or spunlaying processes. (For purposes herein, "oriented along the machine direction" means that the machine direction vector component of the longest dimension of an aperture is greater than the cross direction vector component.) Because of such fiber orientation, this reduces chances that sections of fibers between adjacent apertures along the machine direction will fray or tear away. At the same time, however, while it may be desired in some circumstances that the longest dimension of a majority of the apertures be oriented along the machine direction, it may also be desired that the longest dimension is not parallel with the machine direction. In one example, in which the apertures are elliptical or oval-shaped, it may be desired that their longest dimensions are oriented along angle(s) α between greater than 0 and less than 45 degrees of the machine direction. It will be appreciated that this may add to visual and actual texturing effects, by causing the material along the edges of the apertures to move in a more complex manner in the machine, cross and z-directions as the belt is stretched and moved as during wear. It will also be appreciated that the apertures may be arranged in varying patterns, such as but not limited evenly-spaced and aligned rows and columns, offset rows and columns, diagonal patterns, shaped patterns, etc.

Additionally, the pattern of the apertures may be substantially similar or identical to the pattern of the pre-bonds (if present), in one or more of machine-direction spacing, cross-direction spacing, aperture shape and aperture size. For example, a pattern of pre-bonds may have substantially similar machine and cross direction spacing as the pattern of apertures. Using respective patterns of pre-bonds and apertures that are substantially similar in one or more respects noted can help give the material a more uniform, orderly and/or coherent appearance, and may also help enhance tensile strength as compared with a web in which respective patterns of pre-bonds and apertures do not have such similarities.

Topsheet

The topsheet 11 may be joined to the absorbent core structure 13a and/or the backsheet 12. It should be recognized that other structures, elements, or substrates may be positioned between the core structure 13a and the topsheet 11 and/or backsheet 12. While the topsheet 11, the backsheet 12, and the absorbent core structure 12 may be assembled in a variety of configurations, examples are described generally in U.S. Pat. Nos. 3,860,003; 5,151,092; 5,221,274; 5,554,145; 5,569,234; 5,580,411; and 6,004,306.

The topsheet 11 is generally a portion of the article that may be positioned at least in partial contact or close proximity to a wearer. Suitable topsheets 11 may be manufactured from a wide range of materials, such as porous foams; reticulated foams; apertured plastic films; or woven or nonwoven webs of natural fibers (e.g., wood or cotton fibers), synthetic fibers (e.g., polyester, polyolefin e.g. polyethylene or polypropylene fibers), or a combination of natural and synthetic fibers. The topsheet 11 is generally supple, soft feeling, and non-irritating to a wearer's skin. Generally, at least a portion of the topsheet 11 is liquid pervious, permitting liquid to readily penetrate through its thickness. One topsheet material useful herein is available from BBA Fiberweb, Brentwood, Tenn. as supplier code 055SLPV09U.

Any portion of the topsheet 11 may be coated with a lotion or skin care composition. Examples of suitable lotions include those described in U.S. Pat. Nos. 5,607,760; 5,609,587; 5,635,191; and 5,643,588. The topsheet 11 may be fully or partially elasticized or may be foreshortened so as to provide a void space between the topsheet 11 and the core structure 13a. Exemplary structures including elasticized or foreshortened topsheets are described in more detail in U.S. Pat. Nos. 4,892,536; 4,990,147; 5,037,416; and 5,269,775.

Backsheet

The backsheet 12 is generally positioned to the garment-facing/outward-facing side of the absorbent core structure. Backsheet 12 may be designed to prevent the exudates absorbed by and contained within the pant from soiling articles that may contact the pant, such as bed sheets or outer clothing. In some examples, the backsheet 12 is effectively liquid-impermeable. Suitable backsheet 12 component materials include films such as those manufactured by Tredegar Industries Inc. of Terre Haute, Ind. and sold under the trade names X15306, X10962, and X10964.

The ventilation/breathability effect of including a blouse layer 70 may be further enhanced if backsheet 12 is formed of vapor permeable/breathable web material. In one example, backsheet 12 may be formed of a vapor permeable film, by way of non-limiting example, such as disclosed in U.S. Pat. Nos. 7,307,031; 6,677,258; and 6,429,352. Other suitable backsheet component materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 12 including, but not limited to, surface treatments, particular film selections and processing, particular fiber selections and processing, etc.

Backsheet 12 may also consist of more than one layer. The backsheet 12 may comprise an outer cover and an inner liquid barrier layer. The outer cover may be made of a nonwoven web material. The liquid barrier layer may be made of a substantially liquid-impermeable film. The backsheet may be a laminate of the outer cover and the liquid barrier layer, wherein the layers are held to together, e.g., by a pattern of applied adhesive, e.g., a hot melt adhesive of the type commonly used in the absorbent article manufacturing industry. The surface area of the liquid barrier layer may be smaller than that of the outer cover. In another example the liquid barrier layer may be made of a substantially liquid-impermeable nonwoven, for example, a nonwoven formed at least in part of microfibers or nanofibers having a combination of hydrophobicity and numeric density per unit surface area sufficient to make the nonwoven effectively liquid impermeable under normal use conditions. The outer cover and an liquid barrier layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, various other changes and modifications can be made without departing from the spirit and scope of the invention.

In another alternative, backsheet 12 may be highly vapor permeable yet liquid impermeable because it comprises or is formed of a layer of densely spaced polymeric fine fibers such as disclosed in, by way of non-limiting example, U.S. App. Pub. No. US 2011/0196327.

Absorbent Core Structure

The absorbent core structure 13a includes the entirety of the structure and components thereof disposed between the topsheet and the backsheet, and may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

In one example, at least a portion of the absorbent core structure 13a is substantially cellulose free and contains less than 10% by weight cellulosic fibers, less than 5% cellulosic fibers, less than 1% cellulosic fibers, no more than an immaterial quantity of cellulosic fibers or no cellulosic fibers. It should be understood that an immaterial quantity of cellulosic material does not materially affect at least one of the thinness, flexibility, and absorbency of the portion of the absorbent core structure that is substantially cellulose free. Among other benefits, it is believed that when at least a portion of the absorbent core structure is substantially cellulose free, this portion of the absorbent core structure is significantly thinner and more flexible than a similar absorbent core structure that includes more than 10% by weight of cellulosic fibers. The amount of absorbent material, such as absorbent particulate polymer material present in the absorbent core structure may vary, but in certain embodiments, is present in the absorbent core structure in an amount greater than about 80% by weight of the absorbent core structure, or greater than about 85% by weight of the absorbent core structure, or greater than about 90% by weight of the absorbent core structure, or greater than about 95% by weight of the core. Exemplary absorbent structures for use as the absorbent core structure 13a are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The absorbent core structure 13a and components thereof also may be constructed to provide a system of substantially longitudinally-oriented channels as disclosed in, for example, U.S. application Ser. Nos. 13/491,642; 13/491,644; 13/675,212; 13/709,169; 13/709,244; 13/709,254; and 14/077,355. As noted in the cited applications, a system of one or more substantially longitudinally-oriented channels in the absorbent core structure provides for efficient liquid distribution across the absorbent structure, and also a relatively thinner and more flexible core structure, contributing to an overall sleek, low-bulk, underwear-like look and feel to the pant structure. The channels are grooves or valleys defined through the absorbent material of the core. They may perform at least two functions, including providing passageways along which liquid may rapidly flow to reach and contact surface area of more absorbent material along the length of the absorbent core structure, and providing hinge- or joint-like structures in the absorbent core structure along which the absorbent core structure may more easily flex, providing comfort and bulk-reducing effects.

Cuff Structures

The central chassis may generally have any structure that is suitable for disposable absorbent articles such as diapers and training pants, including any of the absorbent core structure and leg cuff/gasketing structures described and depicted in U.S. application Ser. No. 13/457,521, and including barrier cuffs 15.

Elastic Members

Elastic strands 25 may be formed of an elastomeric material, such as an elastane (for example, LYCRA HYFIT fiber, a product of Invista, Wichita, Kans.). Layers of the pant may be joined together about elastic strands 25 by adhesive deposited between the layers, by thermal bonds, by compression bonds, or by a combination thereof. In other examples, the one or more elastic members may be strips or a section of film formed of elastomeric material.

The elastomeric members can also be formed from various other materials, such as but not limited to, rubbers, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, and other elastomeric materials known in the art, and combinations thereof. In some embodiments, the elastic members can be extruded strand elastics with any number of strands (or filaments). The elastomeric members can have a decitex ranging from 50 to 2000, or any integer value for any decitex value in this range, or any range formed by any of these integer values. The elastomeric members may be in a form of film. Examples of films have been described extensively in prior patent applications (see, for example, U.S. Pat. App. Pub. No. 2010/0040826). The film may be created with a variety of resins combined in at least one of several sublayers, the latter providing different benefits to the film.

During manufacture of pant, the elastic strands 25 or other elastic member(s) may be strained in a lateral direction (relative the pant) by a desired amount as they are being incorporated into the structure. Upon subsequent relaxation of the structure, the elastic member(s) such as elastic strands 25 will contract toward their unstrained lengths. This causes the sandwiching layers to gather and form ruffles or gathers 26 having ridges and valleys extending generally transverse to the direction of pre-strain.

Bending Stiffness

Figure 9:
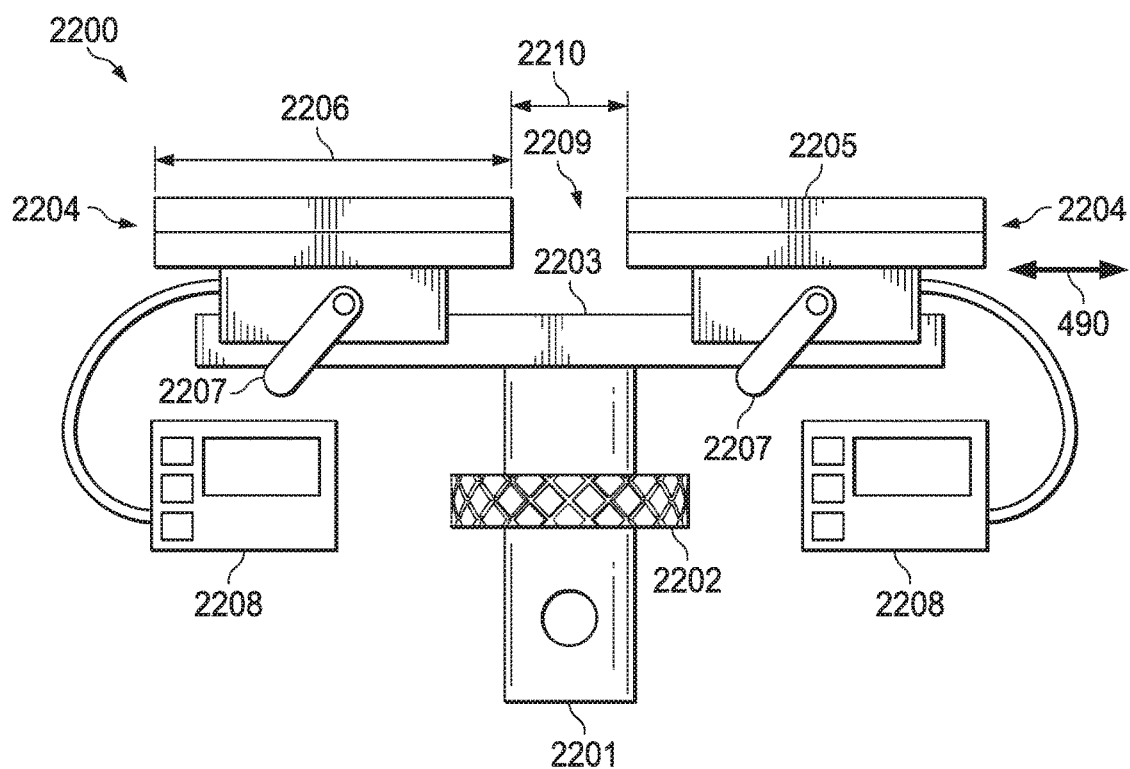
FIG. 9 is a front elevation view of an apparatus for testing the bending stiffness of materials.
Figure 10:
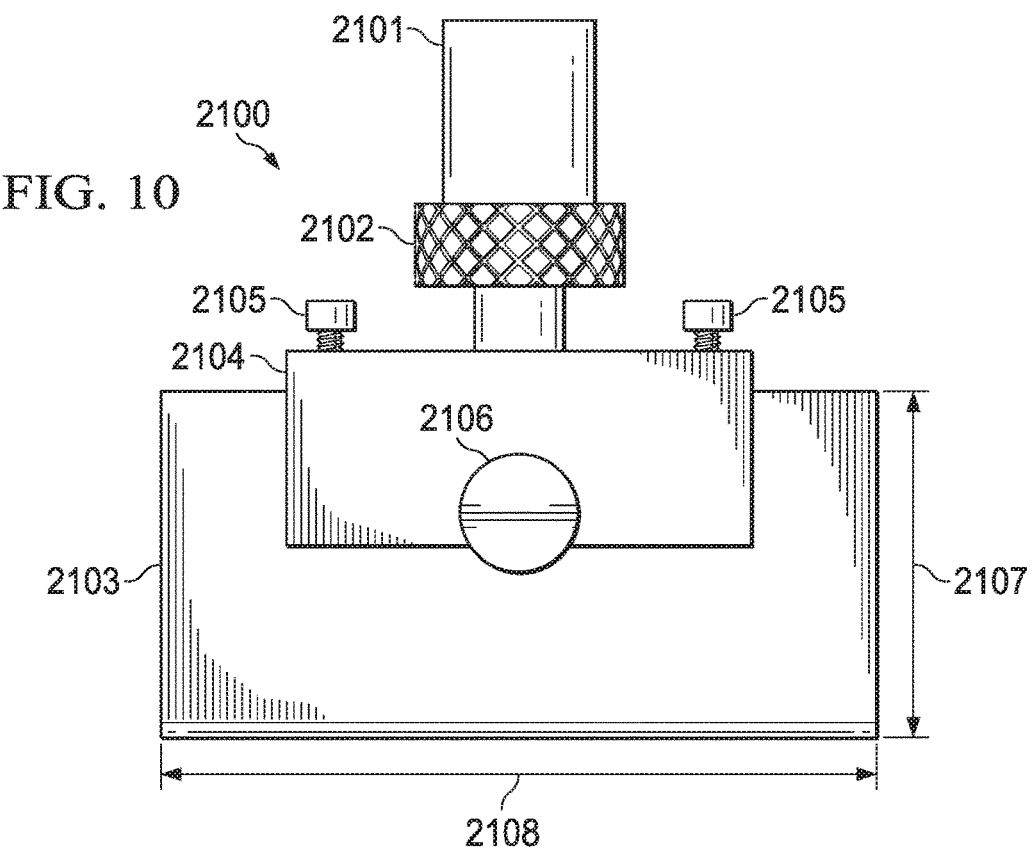
FIG. 10 is a front elevation view showing a plunger for use with the apparatus of FIG. 11.
Figure 11:
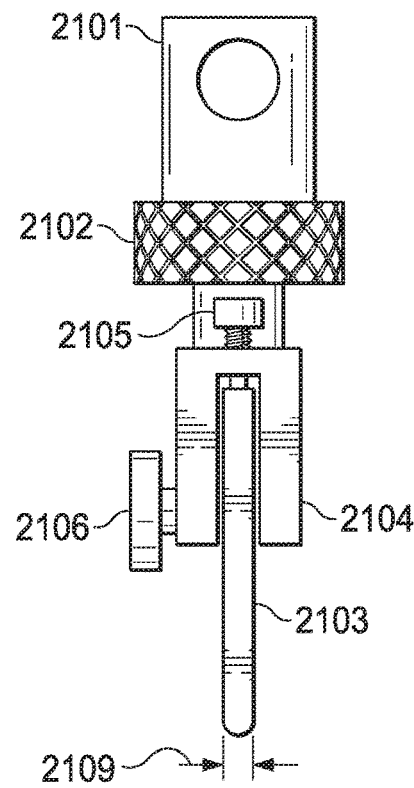
FIG. 11 is a side elevation view showing a plunger for use with the apparatus of FIG. 11.

Bending stiffness of samples from the waistband region and folding region is measured using a constant rate of extension tensile tester with computer interface (a suitable instrument is an MTS Alliance under TestWorks 4 software, as available from MTS Systems Corp., Eden Prairie, Minn.) fitted with a 10 N load cell. A plunger blade 2100, shown in FIG. 10 (front view) and FIG. 11 (side view), is used for the upper movable test fixture. Base support platforms 2200, shown in FIG. 9, are used as the lower stationary test fixture. All testing is performed in a conditioned room maintained at about 23 C±2 C and about 50%±2% relative humidity. Herein, width and length of the test specimen are a lateral width and longitudinal length using the directional conventions corresponding to the fastening member from which the specimen is cut, as "lateral width" and "longitudinal length" are defined herein.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 8.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm.

Set the crosshead to lower at 500 mm/min for a distance of 25 mm. Set the data acquisition rate to 200 Hz.

Precondition specimens at about 23 C±2 C and about 50%±2% relative humidity for 2 hours prior to testing. Die cut a test specimen from the region to be tested, including all layers thereof, 13 mm in width (measured along the lateral direction) by 25.4 mm in length (measured along the longitudinal direction).

Place the specimen flat onto the surface of the support platform 2204 over the gap 2209 with outer/garment-facing surface upward. Center the specimen across the gap; its length should be parallel to the gap width 2210 and its width should be perpendicular to the gap width 2210. Zero the load cell; start the tensile tester and the data acquisition.

Figure 12:
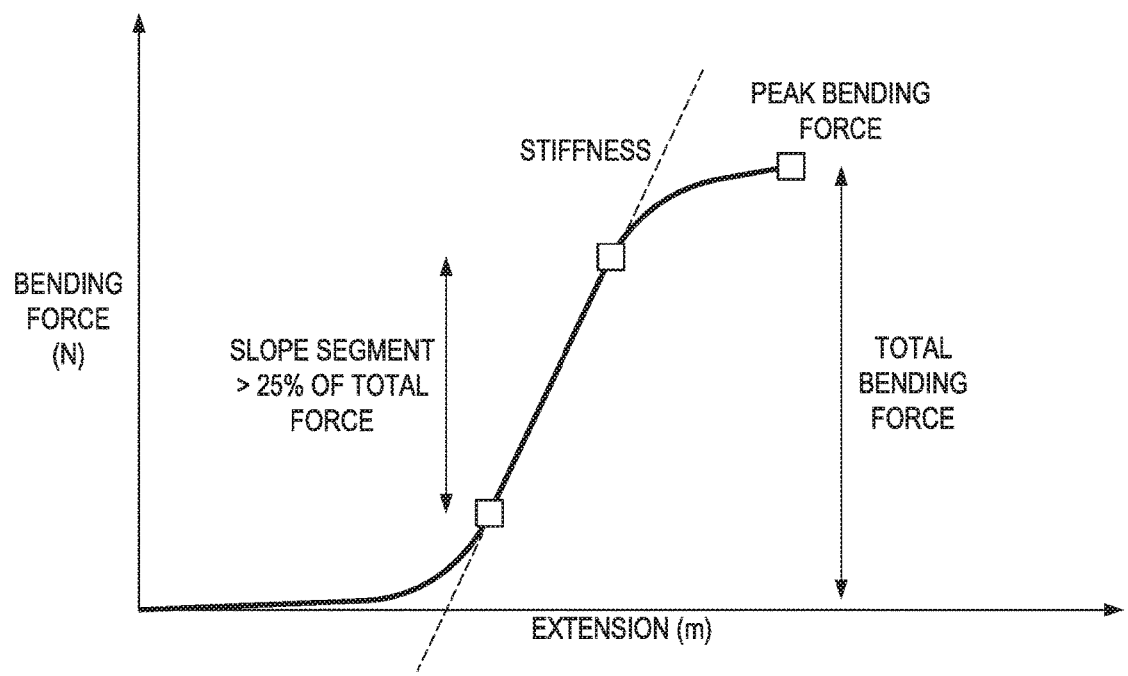
FIG. 12 is a graph showing Peak bending load and slope calculation areas on bending curve.

Program the software to calculate the maximum peak bending force (N) and Stiffness (N/m) from the constructed force (N) verses extension (m) curve. Stiffness is calculated as the slope of the bending force/extension curve for the linear region of the curve (see FIG. 12), using a minimum line segment of at least 25% of the total peak bending force to calculate the slope. If the width of the element is not 13 mm, normalize the actual width to 13 mm as follows:

Stiffness$_{(actual\ width)}$=[Stiffness$_{(13\ mm)}$/13 mm]×actual width (mm)

peak bending force$_{(actual\ width)}$=[peak bending force$_{(13\ mm)}$/13 mm]×actual width (mm)

Report peak bending force to the nearest 0.1 N and the Stiffness to the Nearest 0.1 N/m.

Contraction Ratio

The contraction ratios of samples of the waistband region and folding region are measured as follows:

To obtain samples, specimens 56 mm wide (lateral direction) and 25.4 mm high (longitudinal direction), including all attached layers thereof, are die cut from the respective waistband and folding regions. If specimens of this height are unavailable, use the highest available specimen size, using the same size for each of the waistband region and the foldover region. For purposes herein, the lower edge of the waistband region is defined by the lower edge of an added stiffening layer.

Five specimens are cut from the same portion of identical products for each set. The basis weight of each specimen is measured. Each set is analyzed by the method described below. For the contraction ratio test the lateral direction is test (stretching) direction.

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the sample. The load cell is selected so that the forces measured are between 10% and 90% of the capacity of the load cell used. The initial distance between the lines of gripping force (gauge length) is set at 50.8 mm. The load reading on the instrument is zeroed to account for the mass of the fixture and grips.

The specimen is mounted into the grips in a manner such that there is no slack and the load measured is between 0.00 N and 0.02 N. The specimen is mounted in the center of the grips, such that the specimen direction of stretching is parallel to the applied tensile stress.

The instrument is set up and the specimen mounted as described in the Test Setup above. The contraction ratio test is initiated and the specimen is extended at 508 mm/min, with a data acquisition rate of at least 50 Hertz, until the applied stress reaches 5 N. The contraction ratio is calculated from the length between grip lines L when the applied stress reaches 5 N, and initial gauge length, $L_0$, using the following formula:

$$\text{Contraction ratio} = \frac{L}{L_0}$$

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended that the scope of the invention is limited only by the appended claims and equivalents thereof.

What is claimed is:

1. A disposable absorbent pant, comprising:
an outer chassis having a front waist region having a front waist opening edge, front left and right leg opening edges, and left and right side edges; and a rear waist region having a rear waist opening edge and rear left and right leg opening edges, and left and right side edges;
left and right side seams joining the front waist region and the rear waist region along their respective left and right side edges; and
a central chassis comprising a forward end, a rearward end, a liquid permeable topsheet, a liquid impermeable backsheet, and an absorbent core structure having front and rear ends respectively proximate the forward and rearward ends of the central chassis, and being disposed between the topsheet and the backsheet, the forward and the rearward ends of the central chassis being attached respectively to the front waist region and the rear waist region of the outer chassis,
each of the front and rear waist regions also comprising:
a laterally extending folding region disposed longitudinally between the associated waist opening edge and the proximate front or rear end of the absorbent core structure, the folding region comprising a first web structure;
a waistband region disposed longitudinally between the waist opening edge and the folding region, the waistband region comprising a second web structure having a first one or plurality of laterally extending, pre-strained elastic member(s) disposed between first and second layers, and
a third supplemental layer that is not present in the first web structure, wherein said supplemental layer has a lower lateral edge, and a smallest longitudinal dimension between said lower lateral edge and the proximate front or rear end of the absorbent core structure is no greater than 60 mm;
wherein, for each of the front and rear waist regions, the longitudinal dimension between the waist opening edge and the leg opening edges is at least 30 percent of the overall length of the pant when in an open, fully extended and flattened condition.

2. The pant of claim 1 wherein said smallest longitudinal dimension is no greater than 40 mm.

3. The pant of claim 1 wherein, in each of the front and rear waist regions, the folding region has a first local basis weight and the waistband region has a second local basis weight greater than the first local basis weight.

4. The pant of claim 3 wherein the second local basis weight is at least 30 percent greater than the first local basis weight.

5. The pant of claim 1 wherein the folding region has a first bending stiffness and the waistband region has a second bending stiffness, and the second bending stiffness is greater than the first bending stiffness.

6. The pant of claim 1 wherein at least a portion of the folding region lacks lateral elasticization.

7. The pant of claim 1 wherein each of the front and rear waist regions includes a second one or plurality of laterally extending, pre-strained elastic member(s) disposed between a second pair of layers.

8. The pant of claim 1 wherein the topsheet has a length less than the overall length of the pant in opened and flattened condition.

9. The pant of claim 8 wherein the topsheet does not extend longitudinally into the waistband region in either the front waist region or rear waist region.

10. The pant of claim 8 having a foldover mode wherein the waistband region is folded over to the outside, and down, along the folding region, and wherein the topsheet does not wrap over the fold.

11. The pant of claim 1 wherein one or both the front and rear waist regions comprises a foldover attachment mechanism that permanently or refastenably effects attachment between an upper outside surface of the waistband region and a lower outside surface of the front or rear waist region.

12. The pant of claim 1 having one or more indicia that are most clearly visible from the outside of the pant, and visibly distinguish one or both of the waistband region and the folding region.

13. The pant of claim 1 having one or more indicia on the waistband region that are most clearly visible from the inside of the pant when the waistband region is not folded over, and that are most clearly visible from the outside of the pant when the waistband region is folded over.

14. The pant of claim 1 wherein the waistband region has a first contraction ratio and the folding region has a second contraction ratio, and the first contraction ratio is greater than the second contraction ratio.

15. A disposable absorbent pant, comprising:
an outer chassis having a front waist region having a front waist opening edge, front left and right leg opening edges, and left and right side edges; and a rear waist region having a rear waist opening edge and rear left and right leg opening edges, and left and right side edges;
left and right side seams joining the front waist region and the rear waist region along their respective left and right side edges; and
a central chassis comprising a forward end, a rearward end, a liquid permeable topsheet, a liquid impermeable backsheet, and an absorbent core structure having front and rear ends respectively proximate the forward and rearward ends of the central chassis, and being disposed between the topsheet and the backsheet, the forward and the rearward ends of the central chassis being attached respectively to the front waist region and the rear waist region of the outer chassis,
each of the front and rear waist regions also comprising:
a laterally extending folding region disposed longitudinally between the associated waist opening edge and the proximate front or rear end of the absorbent core structure, the folding region comprising a first web structure;
a waistband region disposed longitudinally between the waist opening edge and the folding region, the waistband region comprising a second web structure having a first one or plurality of laterally extending, pre-strained elastic member(s) disposed between first and second layers, and a third supplemental layer that is not present in the first web structure, wherein the first web structure has a first local basis weight and the second web structure has a second local basis weight that is as least 30 percent greater than the first local basis weight;

wherein, for each of the front and rear waist regions, the longitudinal dimension between the waist opening edge and the leg opening edges is at least 30 percent of the overall length of the pant when in an open, fully extended and flattened condition.

\* \* \* \* \*